US012502552B2

(12) United States Patent
Sjolund et al.

(10) Patent No.: US 12,502,552 B2
(45) Date of Patent: Dec. 23, 2025

(54) TREATMENT PLANNING

(71) Applicant: Elekta AB (publ), Stockholm (SE)

(72) Inventors: Jens Olof Sjolund, Uppsala (SE); Carl Axel Håkan Nordström, Stockholm (SE); John Henry Dahlberg, Stockholm (SE)

(73) Assignee: Elekta AB (publ), Stockholm (SE)

( * ) Notice: Subject to any disclaimer, the term of this patent is extended or adjusted under 35 U.S.C. 154(b) by 179 days.

(21) Appl. No.: 18/576,295

(22) PCT Filed: Jul. 30, 2021

(86) PCT No.: PCT/EP2021/071486
§ 371 (c)(1),
(2) Date: Jan. 3, 2024

(87) PCT Pub. No.: WO2023/006226
PCT Pub. Date: Feb. 2, 2023

(65) Prior Publication Data
US 2024/0316362 A1 Sep. 26, 2024

(51) Int. Cl.
*A61N 5/10* (2006.01)

(52) U.S. Cl.
CPC .................................. *A61N 5/1031* (2013.01)

(58) Field of Classification Search
CPC .... A61N 5/103; A61N 5/1031; A61N 5/1049; A61N 2005/1061; A61N 5/1071; A61N 5/1045; A61N 5/1048; A61N 2005/1041; A61N 5/10; A61B 2034/101; A61B 6/52; A61B 6/545; A61B 2034/104; A61B 6/027; A61B 6/5205
See application file for complete search history.

(56) References Cited

U.S. PATENT DOCUMENTS

| | | | | |
|---|---|---|---|---|
| 7,162,008 B2 * | 1/2007 | Earl | .................... | A61N 5/1031 378/65 |
| 2013/0197878 A1 | 8/2013 | Fiege et al. | | |
| 2021/0016109 A1 | 1/2021 | Sjölund | | |

FOREIGN PATENT DOCUMENTS

| | | | |
|---|---|---|---|
| EP | 3549636 A1 | 10/2019 | |
| WO | WO-2012024448 A2 | 2/2012 | |
| WO | WO-2020177844 A1 | 9/2020 | |
| WO | WO-2023006226 A1 | 2/2023 | |

OTHER PUBLICATIONS

"International Application Serial No. PCT/EP2021/071486, International Search Report mailed Apr. 19, 2022", 5 pgs.
"International Application Serial No. PCT/EP2021/071486, Written Opinion mailed Apr. 19, 2022", 6 pgs.

* cited by examiner

*Primary Examiner* — Don K Wong
(74) *Attorney, Agent, or Firm* — Schwegman Lundberg & Woessner, P.A.

(57) ABSTRACT

The present disclosure relates to the field of radiation therapy and methods, software and systems for treatment planning.

24 Claims, 6 Drawing Sheets

TREATMENT PLANNING

PRIORITY APPLICATIONS

This application is a U.S. National Stage Filing under 35 U.S.C. § 371 from International Application No. PCT/EP2021/071486, filed on Jul. 30, 2021, and published as WO2023/006226 on Feb. 2, 2023; the benefit of priority of which is hereby claimed herein, and which application and publication is hereby incorporated herein by reference in its entirety.

FIELD OF THE DISCLOSURE

The present disclosure relates to the field of radiation therapy and to systems, methods and modules for planning a treatment session of a patient, for example, by means of a radiation therapy system comprising a radiation therapy unit having a fixed radiation focus point. In particular, the present disclosure relates to systems, methods and modules for determining the locations of isocenters in connection with treatment planning.

BACKGROUND

The development of surgical techniques has made great progress over the years. For instance, for patients requiring brain surgery, non-invasive surgery is now available which is afflicted with very little trauma to the patient.

One system for non-invasive surgery is the Leksell Gamma Knife® Perfexion system, which provides such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all or some radiation sources intersect or converge, causing the radiation to reach tissue-destructive levels. The point of convergence is hereinafter referred to as the "focus point".

Treatment plan optimization for radiation therapy, including for example gamma knife radiosurgery, aims at maximizing the dose delivered to the target volume within the patient (e.g. in treatment of tumours) at the same time as the dose delivered to adjacent normal tissues is minimized. In treatment plan optimization, the delivered radiation dose is limited by two competing factors: the first one is delivering a high dose to the target volume and the second one is delivering low dose to the surrounding normal tissues.

An isocenter is defined as a focal point of all beams, and a shot at the given isocenter is defined as the set of sector-collimator combinations with their dwell times used for that isocenter. Selected isocenter locations and their corresponding shots for a given case constitutes a treatment plan. The treatment plan optimization is a process including optimizing the number of shots being used, the sector-collimator combinations, the shot times, and the position of the shot (i.e. isocenter). Clearly, the irregularity and size of a target volume greatly influence the number of shots needed and the size of the shots being used to optimize the treatment. Treatment plans for Leksell Gamma Knife are often designed manually by clinical experts. These manual designs are often challenging and time consuming as the planners are faced with many interdependent decisions. Several researchers have investigated the possibility of automating the treatment planning. Many studies aim to solve the isocenter and shot selection parts separately: first, isocenter locations are chosen based on the geometry of the tumor and nearby organ(s) at risk, or OAR(s); next, the selected isocenters are used as input parameters for the problem of determining shots. The latter problem is known as sector duration optimization (SDO) and can be formulated and solved as a mathematical optimization problem. It has been shown that such models for SDO yield plans with reasonable treatment times and are clinically acceptable provided that isocenters are appropriately chosen. The existing automated isocenter selection methods can be categorized into heuristic and optimization-based approaches. The skeletonization method is one of the existing heuristic isocenter selection methods that aims to extract the so-called object's skeleton, a simplified representation that preserves morphology of the structure and then places isocenters on its joints and at the endpoints.

A pre-requisite in convex plan optimization, i.e. the sector duration optimization (SDO) for the Leksell Gamma Knife, is that the isocenter locations are fixed. Several methods have been proposed over the years to find a viable set of locations. A common feature of all these algorithms is that the target volume is geometrically filled with several 3D shapes that are proxies for real dose distributions of the shots. However, as a result of SDO the dose delivered from each isocenter is a weighted sum of shots; the collimator configuration and the weight of each shot are not known a priori. Therefore, basing isocenter locations on a poor description of dose distributions will irrevocably lead to a sub-optimal solution.

In U.S. Pat. No. 6,201,988, a heuristic optimization procedure is disclosed. Medial axis transformation (so called skeletonization) is used to characterize the target shape and to determine the shot parameters (i.e., position, collimator size and weight). According to U.S. Pat. No. 6,201,988, only skeleton points are considered for potential shot positions and the corresponding shot size is provided by the skeletonization. The shots are represented by spheres and are modeled as discs in filling process. The endpoints of the skeleton are used as start-points in the filling process. However, the treatment plan optimization shown in U.S. Pat. No. 6,201,988 may provide treatment plans having a non-optimal distribution of shot sizes, for example, unnecessarily many small shot sizes may be included leading to many shots being used.

Another heuristic approach is template matching where templates representing compact dose distributions (so called shots) are placed as to touch the target volume periphery, without overlapping other shots too much. When no more such shot positions exist the volume covered so far is treated as non-target, and the procedure is repeated with the reduced target volume. Thus, the target is filled from the surface and inwards, trying to place as large shots as possible at each iteration. This approach is described in the patent U.S. Pat. No. 9,358,404 to Elekta AB. In that patent, an algorithm adapted to SDO is described, making no presumptions on specific dose distributions, determines isocenter positions according to two separate geometrical attributes of the target: the local surface curvature and the skeleton. The algorithm places more isocenters close to high curvature surface regions than in low curvature regions to enable a conformal dose distribution. It also takes the morphological properties into account and place isocenters on the skeleton. For large targets, regions that are neither close to the surface nor the medial axis are iteratively filled with isocenters furthest away from already placed isocenters.

Recent advances in the field of artificial intelligence has motivated the exploration of so called knowledge-based methods. For instance, there are newly developed methods utilizing a moment-based shape description of tumors and isocenters in a neural network based prediction model of isocenter placement (Berdyshev et al., 2020). These methods require large training sets because of the inter-variability between users in placing isocenters for a given volume and also training sets that are indication specific. The input data to these methods are already delivered plans with a single shot at each isocenter.

In alternative methods, excessively many isocenters are proposed initially and then a first optimization problem is solved to reduce the isocenters to a manageable number, which are then used in subsequent optimizations. However, because the complexity of the optimization problem grows quickly in the number of isocenter locations, it would take huge computational resources (time and memory) to solve the first optimization problem. This approach is described in the U.S. Pat. No. 10,744,343.

Hence, there is a need of more efficient methods for planning the treatment and for optimizing the treatment planning. In order to reach high quality treatment plans it is paramount that the set of isocenter locations provides sufficient freedom to capture clinically relevant tradeoffs. On the other hand, the number of isocenter locations has an immediate and quite drastic effect on the optimization time. Thus, there is a need for improved methods that generates a set of isocenter locations that balances these competing demands.

SUMMARY

An object of the present disclosure is to provide more efficient methods, systems and modules for planning the treatment and thus for optimizing the treatment planning.

A further object of the present disclosure is to provide more efficient methods, systems and modules for determining geometric configurations during a treatment planning procedure, for example isocenter positions or seed positions in a target volume or the beam orientation of radiation fields.

These and other objects are fulfilled by the present disclosure as defined by the independent claims. Preferred embodiments are defined by the dependent claims.

The term “target volume” refers to a representation of a target of a patient to be treated during radiation therapy. The target may be a tumour to be treated with radiation therapy. Typically, the representation of the target is obtained by, for example, non-invasive image captured using X-ray or NMR.

The term “shot” refers to a delivery of radiation to a predetermined position within a target volume having a predetermined level of radiation and a spatial distribution. The shot is delivered during a predetermined time (“beam-on” time) via at least one sector of the collimator of the therapy system using one of the states of the sector. A “composite shot” refers to the delivery of radiation to a focus point using different collimator sizes for different sectors.

The term “beam-on time” refers to the predetermined time during which a shot is delivered to the target volume.

The term “overlapping” means that, in viewing the shots as 3-D volumes (defined as the volume with dose above a selected threshold, e.g. the 50% isodose level), a shot volume overlaps or intersects other shot volumes.

The present disclosure can, for example, be used in radiation therapy or radiotherapy. Radiotherapy is used to treat cancers and other ailments in the tissue of humans and other mammals. One such radiotherapy device or a radiation therapy device is a Gamma Knife, which irradiates a patient with many low-intensity gamma rays that converge with high intensity and high precision at a target (e.g., a tumour). Another radiotherapy device uses a linear accelerator, which irradiates a tumour with high-energy particles (e.g., photons, electrons, and the like). Still another radiotherapy device, a cyclotron, uses protons and/or ions. The direction and shape of the radiation beam should be accurately controlled to ensure that the tumour receives the prescribed radiation dose, and the radiation from the beam should minimize damage to the surrounding healthy tissue, especially the OARs. Treatment planning can be used to control radiation beam parameters, and a radiotherapy device effectuates a treatment by delivering a spatially varying dose distribution to the patient.

The present disclosure is for example used in connection with treatment planning of treatment provided by means of a radiation therapy systems having a collimator body provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

A planning process generally involves the designation (mapping, non-invasive image capturing, as for example by X-ray or NMR) of a target volume for radiation therapy, fill the target, without extending high-dose areas too much outside the target, determining a level of radiation which is therapeutically effective when directed into volumes of the target which are to be treated, determining a distribution of shots or doses of radiation which can be directed into the target such that radiation of each shot which exceeds a predetermined percentage of the level of radiation which is therapeutically effective by more than a fixed percentage of each shot of the radiation, is not directed at areas outside the target.

The present disclosure takes a new and different approach to treatment planning.

According to a first and general aspect of the present disclosure, there is provided a method for radiotherapy treatment planning comprising: selecting subsets of treatment related data from treatment planning data; creating a treatment plan model from the subsets of treatment related data; processing the treatment plan model to generate a set of geometric configurations, wherein the processing includes estimating subsets of treatment parameters that maximize a treatment quality criterion in at least two phases, said treatment quality criterion being based on the treatment plan model; and processing the set of geometric configurations to create a radiotherapy treatment plan.

According to another aspect of the present disclosure, there is provided computer-readable medium having stored therein computer-readable instructions for a processor, wherein the instructions when read and implemented by the processor, cause the processor to select subsets of treatment related data from treatment planning data, create a treatment plan model from the subsets of treatment related data, process the treatment plan model to generate a set of geometric configurations (e.g., isocenter locations), wherein the processing includes estimating subsets of treatment parameters that maximize a treatment quality criterion in at least two phases, said treatment quality criterion being based on the treatment plan model, and process the set of geometric configurations to create a radiotherapy treatment plan. In an embodiment, the treatment plan model is processed using a supervised or unsupervised machine learning model, such as a neural network.

The present disclosure is generally based on machine learning for isocenter generation. At the highest level, an abstract measure of plan quality is modelled by using a treatment quality criterion or utility criterion. However, the utility criterion is often computationally inconvenient, and therefore, it is maximized approximately. A bit more concretely, for a Gamma Knife embodiment, the utility criterion would quantify the expected merit (over all planner preferences) of the combination of a dose distribution and the corresponding treatment complexity (mainly beam-on time). But it's infeasible to search over all dose distributions, which are parameterized by isocenter locations and corresponding beam-on times (i.e. the arguments). Thus, arguments that maximize the utility criterion are estimated in a two-stage procedure: first generating isocenter locations, then determining beam-on times with isocenter locations fixed.

According to embodiments of the present disclosure, the treatment quality criterion reflects a quantification of expected merits of different combinations of treatment parameters for selected treatment planning variables.

In embodiments of the present disclosure, the selected treatment planning variables include treatment planning preferences.

According to embodiments of the present disclosure, the step of creating a treatment plan model comprises using at least one of a model of radiation dose deposition or a model of treatment planning preferences for said treatment plan model.

In further embodiments of the present disclosure, the step of processing the set of geometric configurations further comprises formulating a radiotherapy optimization problem based on the generated geometric configurations, and estimating a solution to said radiotherapy optimization problem using said generated geometrical configurations. In an embodiment, the machine learning model is trained based on a loss function that includes or uses the radiotherapy optimization problem or variant thereof.

According to embodiments of the present disclosure, the step of processing the set of geometric configurations further comprises a first phase where geometric configurations are generated, and a second phase where said radiotherapy problem is solved for fixed geometrical locations.

In further embodiments of the present disclosure, the treatment quality criterion comprises at least one of a dose-based criterion and a radiotherapy optimization problem. In an embodiment, the machine learning model is trained to minimize a loss function or maximize a loss function that includes the treatment quality criterion.

According to embodiments of the present disclosure, the processing includes using a parameterized method including determining a subset of the parameters based on a training set of treatment plan models.

Yet other embodiments of the present disclosure includes organizing the parameterized method in a directed graph.

According to embodiments of the present disclosure, the step of determining a subset of the parameters based on a training set of treatment plan models comprises optimizing a loss function.

In embodiments of the present disclosure, the loss comprises at least one of the treatment quality criterion, a regularization term, a dose metric, a fluence metric, a merit function of a radiotherapy optimization problem or the optimal value of a radiotherapy optimization problem. Furthermore, the loss can be differentiable or subdifferentiable, and the step of optimizing the loss function comprises evaluating gradients or subgradients of the loss function. In an embodiment, the machine learning model is trained based on training data to generate the geometric configurations and then parameters of the machine learning model are updated based on a loss that is computed as a function of the generated geometric configurations.

According to embodiments of the present disclosure, the training set of treatment plan models includes treatment plan models created from non-clinical treatment related data. This training set can be used to train the machine learning model in a supervised or unsupervised approach.

In embodiments of the present disclosure, the training set of treatment plan models comprises geometric configurations. In such cases, the machine learning model predicts a set of geometric configurations from the training set or batch of training data and a loss is computed based on a deviation between the predicted set of geometric configurations and ground-truth geometric configurations provided in the training set or batch of training data. Parameters of the machine learning model are then updated based on the deviation and the updated machine learning model is applied to a new batch of training data. This process can be repeated a number of times or over multiple batches of training data until a stopping criterion is met. At that point, a trained machine learning model is provided and used to generate the geometric configurations.

According to embodiments of the present disclosure, the subsets of treatment related data in the training set of treatment plan models is restricted to the same kind of data the processed treatment plan model is based on.

In embodiments of the present disclosure, the selected subsets of treatment related data from treatment planning data comprises at least one of medical images, structure sets, dose distributions, dose preferences, optimization preferences, medical condition, or geometric configurations. In some embodiments, the selected subsets of treatment related data from treatment planning data comprises arbitrary dimension and/or multiple types of data (e.g., continuous, ordinal, discrete, and the like). In some embodiments, the selected subsets of treatment related data from treatment planning data comprises a distance to pre-determined anatomical regions, such as target volume(s) or the OAR(s) or the patients surface. In some examples, the selected subsets of treatment related data from treatment planning data comprises a signed distance (closest distance in any direction) or directed distance field (closest dimension-wise distance) between a volume (e.g., a voxel) and closest anatomical region, such as a target volume or the surface of the body part in the medical image, which can also be represented as voxels. Distances to multiple regions of interest can also be Included in the selected subsets of treatment related data from treatment planning data. In some embodiments, the selected subsets of treatment related data from treatment planning data comprises global information, such as spatial coordinates of an anatomical region or a probability that an anatomical region includes a particular tissue type. In some embodiments, the selected subsets of treatment related data from treatment planning data comprises features derived from a convolution of images with at least one linear filter (e.g., local phase, gradients, edge, or corner detectors). In some embodiments, the selected subsets of treatment related data from treatment planning data comprises features derived by a transformation of one or more images (e.g., Fourier transform, Hilbert transform, Radon transform, distance transform, discrete cosine transform, wavelet transform, and the like).

In some embodiments, the selected subsets of treatment related data from treatment planning data comprises information based on "information theoretical measures" (e.g., mutual information, normalized mutual information, entropy, Kullback-Leibler distance, and the like). In some embodiments, the selected subsets of treatment related data from treatment planning data comprises a feature descriptor providing a higher-dimensional representation as used in the field of computer vision, such feature descriptor may include characteristics of a particular voxel of the image, such as SIFT (Scale-invariant feature transform), SURF (Speeded Up Robust Features), GLOH (Gradient Location and Orientation Histogram), or HOG (Histogram of Oriented Gradients). In another embodiment, the covariance/correlation between a plurality of image regions (e.g., two or more voxels) can be captured using a higher-dimensional representation. In some embodiments, the selected subsets of treatment related data from treatment planning data comprises, for example, patient information such as age, gender, tumor size, a responsible physician and the like. In another embodiment, the selected subsets of treatment related data from treatment planning data comprises patient specific information, responsible physician, organ or volume of interest segmentation data, functional organ modeling data (e.g., serial versus parallel organs, and appropriate dose response models), radiation dosage (e.g., also including dose-Volume histogram (DVH) information), lab data (e.g., hemoglobin, platelets, cholesterol, triglycerides, creatinine, sodium, glucose, calcium, weight), vital signs (blood pressure, temperature, respiratory rate and the like), genomic data (e.g., genetic profiling), demographics (age, sex), other diseases affecting the patient (e.g., cardiovascular or respiratory disease, diabetes, radiation hypersensitivity syndromes and the like), medications and drug reactions, diet and lifestyle (e.g., smoking or non-smoking), environmental risk factors, tumor characteristics (histological type, tumor grade, hormone and other receptor status, tumor size, vascularity cell type, cancer staging, gleason score), previous treatments (e.g., surgeries, radiation, chemotherapy, hormone therapy), lymph node and distant metastases status, genetic/protein biomarkers (e.g., such as MYC, GADD45A, PPM1D, BBC3, CDKN1A, PLK3, XPC, AKT1, RELA, BCL2L1, PTEN, CDK1, XIAP and the like), single nucleotide polymorphisms (SNP) analysis (e.g., XRCC1, XRCC3, APEX1, MDM2, TNFR, MTHFR, MTRR, VEGF, TGFB, TNFC), texture descriptors (e.g., representations learned from deep learning), and the like.

According to embodiments of the present disclosure, the treatment plan model is probabilistic. In such cases, the machine learning model is a generative model that generates the geometric configurations in a way that results in a criterion that has a similar distribution as a distribution of the treatment plan model.

In embodiments of the present disclosure, the set of geometric configurations includes at least one of an isocenter location, a beam orientation or a seed position, such as in brachytherapy.

Further embodiments of the present disclosure includes selecting subsets of treatment related data from treatment planning data, creating a treatment plan model from the subsets of treatment related data including defining a latent state model representing encoded geometrical locations, processing the treatment plan model to generate a set of geometric configurations, including determining isocenter locations in a target volume, determining a predicted dose distribution based on the generated set of geometric locations, evaluating the predicted dose distribution with respect to evaluation conditions, defining the evaluation conditions to include the selected subsets of treatment related data, for example, the evaluation conditions includes evaluating predicted dose distribution as output with respect to selected treatment data as input, and selecting the generated set of geometric locations if evaluation conditions are satisfied. However, the selected input could be a dose distribution (e.g. an ideal) to be matched by the predicted dose distribution, it might also be separated (boundary) conditions based on e.g. prescription dose, maximum OAR dose, geometry etc. that penalize any over respectively under shooting of predicted dose distribution. Note that the latter may allow for inputting disjointed sets of treatment data (possibly of different signs) unlike a dose distribution.

In embodiments of the present disclosure, the processing of the treatment plan model comprises receiving a set of geometric configurations and generating at least one new geometric configuration. In an embodiment, the new geometric configuration is generated using a trained machine learning model.

Yet other embodiments of the present disclosure comprise evaluating the utility criterion based on the generated geometric configuration and predetermined evaluation conditions, and, if conditions are not fulfilled, generating at least one further geometric location.

According to embodiments of the present disclosure the utility criterion or treatment quality criterion includes expected future values of utility criteria.

In embodiments of the present disclosure, the method for generating at least one new configuration uses at least one of optimal control, dynamic programming, supervised learning, unsupervised learning, or reinforcement learning.

In some embodiments, the method is a discrete-time sequential decision process comprising taking actions and receiving rewards from the environment. The action space may be discrete, e.g. choosing geometric configurations from a predefined set, or continuous, e.g. choosing coordinates or angles in a continuous region. At a given instance in time, the state of the process refers to the complete information that may be used to inform the next decision. The environment may be based on the treatment plan model. The environment also gives rise to rewards, special numerical values that may be based on the utility criterion or treatment quality criterion but may comprise further components that guide the sequential decision process, e.g. regularization or priors.

The actions influence not just immediate rewards, but also subsequent states, and through those future rewards. This process may be formalized as e.g. a Markov Decision Process (MDP). To guide action selection, it is vital to accurately assign credit for long-term consequences. In some embodiments, the method performs this credit assignment by estimating the value of state-action pairs, and in other embodiments by estimating the value of a state given optimal action selection. In some embodiments, the state-action pairs or value function may be estimated using a machine learning method, e.g. a neural network.

The dynamics of the MDP describe how taking a given action in a given state leads to the next state and the emission of a reward. The dynamics may be deterministic or probabilistic. Further, the dynamics may be known, partially known, or unknown. In some embodiments, when the dynamics are known, the optimal action may be selected using dynamic programming. In other embodiments, reinforcement learning may be used to select an approximately optimal action. In other embodiments, given a (potentially approximate) model of the dynamics, optimal control may be used to select an approximately optimal action.

As the skilled person realizes, steps of the methods according to the present disclosure, as well as preferred embodiments thereof, are suitable to realize as computer program or as a computer readable medium.

Further objects and advantages of the present disclosure will be discussed below by means of exemplifying embodiments.

DETAILED DESCRIPTION OF THE DRAWINGS

With reference first to FIG. 1*a*-2*b*, exemplary radiation therapy devices in which a treatment plan developed using the present disclosure can be used for treatment of a patient. The present disclosure may be used in radiation therapy device using a linear accelerator, which irradiates a tumour with high-energy particles (e.g., photons, electrons, and the like). Still another radiation therapy device, a cyclotron, uses protons and/or ions.

Figure 1A:
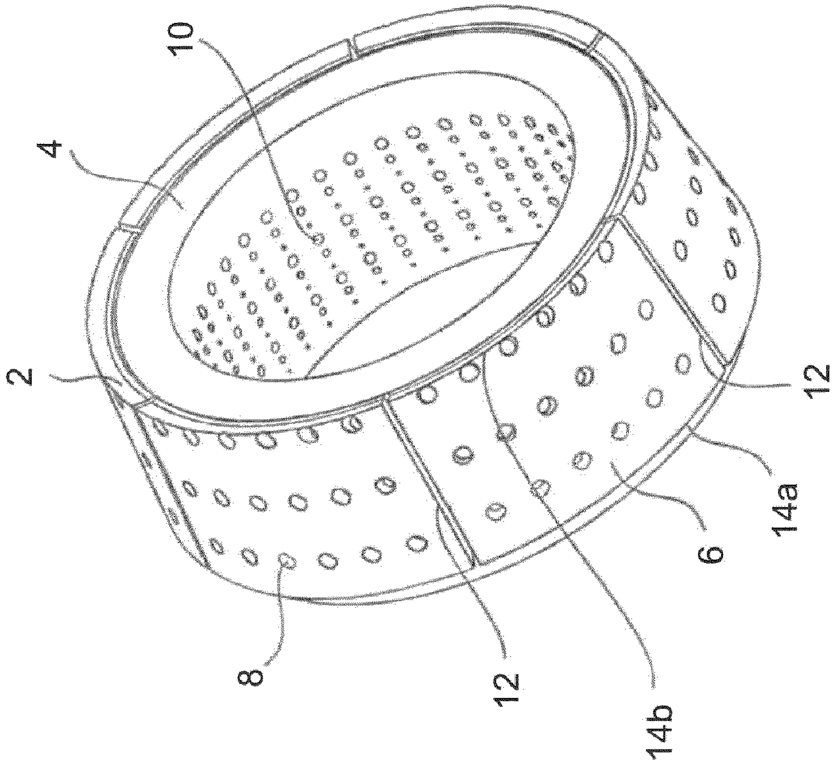
FIG. 1*a* is a perspective view of an assembly comprising a source carrier arrangement surrounding a collimator body in which the present disclosure may be used.
Figure 1B:
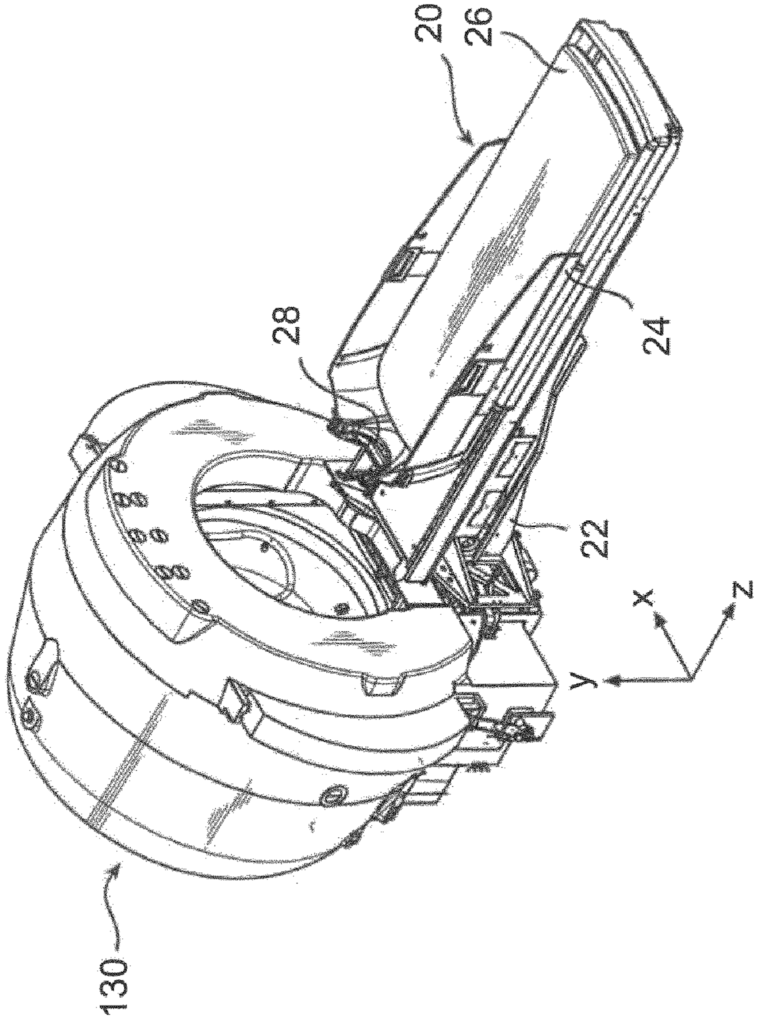
FIG. 1*b* shows a radiation therapy device in which the assembly of FIG. 1 may be used.

With reference first to FIGS. 1*a* and 1*b*, an exemplary radiation therapy device in which a treatment plan developed using the present disclosure can be used for treatment of a patient.

FIG. 1*a* is a perspective view of an assembly comprising a source carrier arrangement 2 surrounding a collimator body 4. The source carrier arrangement 2 and the collimator body 4 both have the shape of a frustum of a cone. The source carrier arrangement 2 comprises six segments 6 distributed along the annular circumference of the collimator body 4. Each segment 6 has a plurality of apertures 8 into which containers containing radioactive sources, such as cobalt, are placed. The collimator body 4 is provided with collimator passages or channels, internal mouths 10 of the channels are shown in the figure.

Each segment 6 has two straight sides 12 and two curved sides 14*a*, 14*b*. One of the curved sides 14*a* forms a longer arc of a circle, and is located near the base of the cone, while the other curved side 14*b* forms a shorter arc of a circle. The segments 6 are linearly displaceable, that is they are not rotated around the collimator body 4, but are instead movable back and forth along an imaginary line drawn from the center of the shorter curved side 14*b* to the center of the longer curved side 14*a*. Such a translation displacement has the effect of a transformation of coordinates in which the new axes are parallel to the old ones.

As can be seen from FIG. 1*a* there is a larger number of internal mouths 10 or holes of the collimator passages than the number of apertures 8 for receiving radioactive sources. In this particular case there are three times as many collimator passages as there are apertures for receiving radioactive sources, such as e.g. 180 apertures and 540 collimator passages. The reason for this is that there are three different sizes of collimator passages in the collimator body 4, or rather passages which direct radiation beams with three different diameters, toward the focus. The diameters may e.g. be 4, 8 and 16 mm. The three different types of collimator passages are each arranged in a pattern which corresponds to the pattern of the apertures in the source carrier arrangement. The desired size or type of collimator passage is selected by displacing the segments 6 of the source carrier arrangement linearly along the collimator body so as to be in register with the desired collimator passages.

In FIG. 1*b*, a radiation therapy system including a radiation therapy device 130 having a source carrier arrangement as shown in FIG. 1*b*, and a patient positioning unit 20 is shown. In the radiation therapy device 130, there are thus provided radioactive sources, radioactive source holders, a collimator body, and external shielding elements. The collimator body comprises a large number of collimator channels directed towards a common focus point, as shown in FIG. 1*b*.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit or interface unit. The coordinates of the fixation unit are defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system.

Figure 2A:
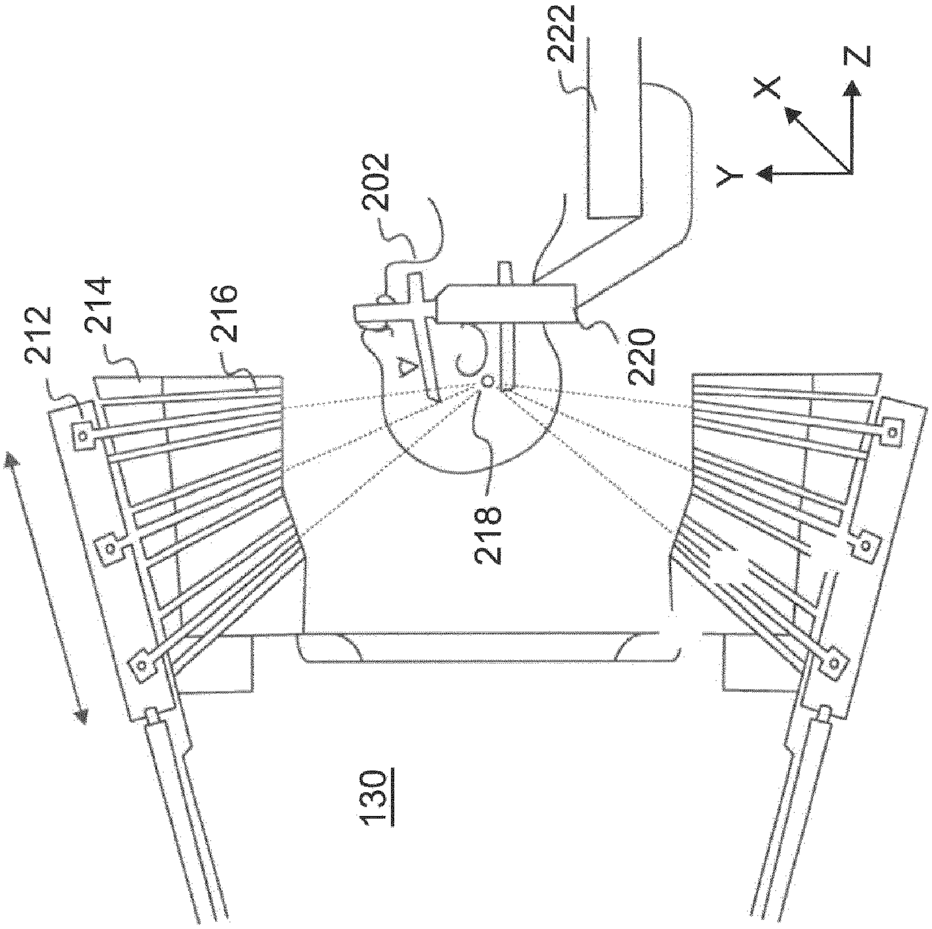
FIG. 2*a* shows a radiation therapy device, a Gamma Knife, in which the present disclosure may be used.

FIG. 2*a* illustrates a radiation therapy (radiotherapy) device 130, a Gamma Knife in which the present disclosure can be used. A patient 202 may wear a coordinate frame to keep stable the patient's body part (e.g. the head) undergoing surgery or radiotherapy. Coordinate frame and a patient positioning system 222 may establish a spatial coordinate system, which may be used while imaging a patient or during radiation surgery. Radiation therapy device 130 may include a protective housing to enclose a plurality of radiation sources 212 for generation of radiation beams (e.g., beamlets) through beam channels 216. The plurality of beams may be configured to focus on an isocenter 218 from different locations. While each individual radiation beam may have relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

Figure 2B:
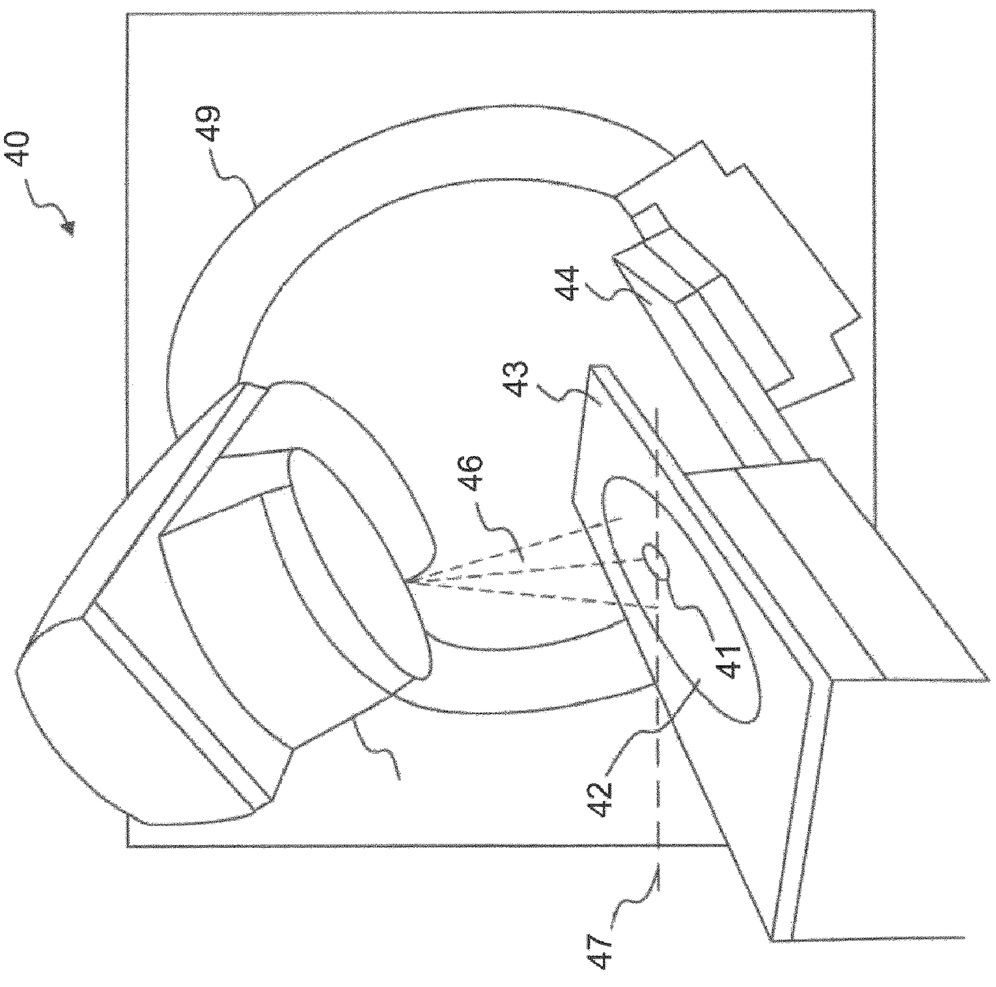
FIG. 2*b* shows another radiotherapy device, a linear accelerator, in which the present disclosure can be used.

FIG. 2*b* illustrates another radiotherapy device, a linear accelerator 40 in which the present disclosure can be used. Using a linear accelerator, a patient 42 may be positioned on a patient table 43 to receive the radiation dose determined by the treatment plan. Linear accelerator 40 may include a radiation head 45 that generates a radiation beam 46. The entire radiation head 45 may be rotatable around a horizontal axis 47. In addition, below the patient table 43 there may be provided a flat panel scintillator detector 44, which may rotate synchronously with radiation head 45 around an isocenter 41. The intersection of the axis 47 with the center of the beam 46, produced by the radiation head 45 is usually referred to as the "isocenter". The patient table 43 may be motorized so that the patient 42 can be positioned with the tumor site at or close to the isocenter 41. The radiation head 45 may rotate about a gantry, to provide patient 42 with a plurality of varying dosages of radiation according to the treatment plan. In some cases, the set of gantry positions and corresponding directions from which radiation is delivered, can include the relevant geometric configurations addressed by the disclosed techniques.

The methods according to the present disclosure are generally based on machine learning (using a machine learning model) for isocenter generation. In one approach a machine learning model, such as a neural network, is trained where a dose distribution is input and the method predicts the underlying set of isocenters that produced it. This could be seen as a form of deconvolution, especially if the prediction is formatted as a heat map, i.e. an image where the pixel intensity corresponds to the irradiation time of an isocenter at that pixel. The training loss could be, for instance, the L2 loss in the space of isocenters or in the space of doses (since the dose kernels can be computed the dose is given by a linear combination of the isocenter times). At test time, one would input a desired dose distribution and use the predicted isocenter in the subsequent optimization.

The machine learning learning model can be a supervised machine learning model or unsupervised machine learning model. Supervised machine learning (ML) algorithms or ML models or techniques can be summarized as function approximation. Training data consisting of input-output pairs of some type (e.g., one or more training optimization variables and training parameters of a plurality of training radiotherapy treatment plan optimization problems) are acquired from, e.g., expert clinicians or prior optimization plan solvers and a function is "trained" to approximate this mapping. Some methods involve neural networks (NNs). In these, a set of parametrized functions $A_\theta$ are selected, where $\theta$ is a set of parameters (e.g., convolution kernels and biases) that are selected by minimizing the average error over the training data. If the input-output pairs are denoted by $(x_m, y_m)$, the function can be formalized by solving a minimization problem such as the below Equation:

$$\min_\theta \sum_{m=1}^{M} \|A_\theta(x_m) - y_m\|^2$$

Once the network has been trained (e.g., $\theta$ has been selected), the function $A_\theta$ can be applied to any new input. For example, in the above setting of a never-before-seen radiotherapy treatment plan can be fed into $A_\theta$, and one or more sets of isocenters (e.g., geometric configurations) are estimated that match what an optimization problem solver would find.

Simple NNs consist of an input layer, a middle or hidden layer, and an output layer, each containing computational units or nodes. The hidden layer(s) nodes have input from all the input layer nodes and are connected to all nodes in the output layer. Such a network is termed "fully connected." Each node communicates a signal to the output node depending on a nonlinear function of the sum of its inputs. For a classifier, the number of input layer nodes typically equals the number of features for each of a set of objects being sorted into classes, and the number of output layer nodes is equal to the number of classes. A network is trained by presenting it with the features of objects of known classes and adjusting the node weights to reduce the training error by an algorithm called backpropagation. Thus, the trained network can classify novel objects whose class is unknown.

Neural networks have the capacity to discover relationships between the data and classes or regression values, and under certain conditions, can emulate any function including non-linear functions. In ML, an assumption is that the training and test data are both generated by the same data-generating process, in which each sample is identically and independently distributed. In ML, the goals are to minimize the training error (e.g., minimize a loss function) and to make the difference between the training and test errors as small as possible. Underfitting occurs if the training error is too large; overfitting occurs when the train-test error gap is too large. Both types of performance deficiency are related to model capacity: large capacity may fit the training data very well but lead to overfitting, while small capacity may lead to underfitting.

Another approach is to train a generative machine learning model which attempts to generate isocenter locations from the same distribution as the training data. In practice, this could be done using e.g. variational inference or a Generative Adversarial Network (GAN). A further approach is to replace a first optimization with a (fast) prediction method, which has been trained to predict which isocenter locations that survives the first optimization. Yet another approach is to design a method where the loss function does not make use of any prior information on where isocenters have been located. For example, the loss function may only depend on geometrical properties, or use a simple dosimetric model (e.g. templates) to evaluate the loss. In one embodiment, the loss function is either the same objective function as in the treatment plan optimization problem, e.g. as described in U.S. Pat. No. 10,744,343, or a surrogate that approximates this objective function. Such an approach can be generalized to any optimization problem that it is possible to differentiate through, which includes all convex optimization problems. Provided with a differentiable method for computing (or approximating) dose rate kernels from the isocenter locations, this means that gradient-based end-to-end training may be performed by including the optimization problem in the loss function. Examples of such dose calculation methods have been described in the earlier U.S. Patent Application Publication Nos. 2020/0254277 and 2021/0016109 and includes e.g. a convolution with an appropriate kernel or a pre-trained neural network (NN).

According to another embodiment, the fill algorithm could be improved by making its parameters target specific. For instance, a machine learning algorithm could be used to predict a suitable set of parameters. Another embodiment could be to use an autoencoder (AE), i.e. auto-associative network, to map some input geometry or dose distribution to itself, through a latent state representing the encoded isocenters. This way, predetermined isocenters are not needed as ground truth. Further on, the model might be forced to discover a naturally minimal spatial representation of the distribution, loosing as little information as possible, to find sufficiently small but necessarily large set of isocenters to provide shorter beam on time while ensuring good clinical quality. The input could correspond to dose distributions generated from cases with the optimizer, U.S. Pat. No. 10,744,343, that represents the true shape in terms of what can be delivered and has the same quality as the current benchmark. Nevertheless, the data will be biased towards the underlying isocenters used by the optimizer. Another alternative is to use an ideal dose distribution, i.e. equivalently the weighted geometry corresponding to the prescription dose, ring weight penalization, max OAR dose and low dose weight. This will cause a discrepancy from the predicted distribution, which will be forced to be expressed in a physically feasible way, meaning a smooth multimodal distribution so that it can be delivered. However, the prediction is hypothesized to converge in a direction towards the ideal distribution, which in practice will take shape similarly of the predicted distribution. Thus, even if usage of the optimized dose distribution can theoretically lead to a zero loss (regularization put aside) unlike the discrepancy of ideal input, the latter may have better quality in terms of clinical metrics. On top of that, the encoder part of the latter approach would be the final recipe for generating isocenters from geometry definitions in the prediction step. Moving on to the hidden parts, there is a large degree of freedom in designing the encoding layers. The latent space, representing the isocenters, and its decoding should however be more carefully designed to capture an accurate spatial representation respectively be decoded in a way to be physically feasible. For a vanilla AE, the isocenters could be independent coordinate points (one neuron per dimension or a one-hot-grid). Then there would be a fixed number of channels for each isocenter (regularization is needed to avoid redundancy), followed by radial basis function activation (e.g. gaussians), or convolutional layers to mirror the dose engine. The latent layer could also be a probabilistic occupancy grid, with number of channels corresponding to number of Degrees of Freedom (DoF), i.e. collimator configurations. In the case of using a variational AE (VAE), the latent state would be separated into a probabilistic distribution followed by a sampled representation of isocenters. Usage of VAE tend to structure the latent representation better than a vanilla AE, note however that it would have a prior assumption of Gaussian distributions. Finally, the predicted output will be compared with the geometrical thresholds with some norm or optimization cost function as well as some regularization (e.g. L1 for vanilla AE or Kullback divergence for VAE) to compute loss.

As an example, the ML model trained to be applied and provide a set of geometric configurations is trained in one implementation according to supervised learning techniques. In such cases, to train the ML model, a plurality of training data that includes previous treatment plans and corresponding known or ground truth geometric configurations for other patients (and/or that include synthetically generated data) are retrieved. The ML model is applied to a first batch of training data to estimate a given set of geometric configurations. The output or result of the ML model is compared with the corresponding training data (e.g., the ground truth geometric configurations) of the first batch of training data and a deviation is computed between the output or result and the corresponding training data using a loss function. As another example, the output or result of the ML model can be used to solve an optimization problem to compute a dose metric or dosimetric criterion. The dose metric or dosimetric criterion can be measured against a target criterion to compute a loss or deviation.

Based on the deviation computed using the loss function (s), updated parameters for the ML model are computed. The ML model is then applied with the updated parameters to a second batch of training data to again estimate a given set of geometric configurations for comparison with the parameters previously determined for the second batch of data. Parameters of the ML model are again updated and iterations of this training process continue for a specified number of iterations or epochs or until a given convergence criteria has been met.

In an example, the ML model trained to be applied and provide a closed form solution is trained in one implementation according to unsupervised learning techniques, wherein the true solution is not used (regardless of whether it's known or not). In such cases, to train the ML model, a plurality of training treatment plans for other patients (and/or that include synthetically generated problems) are retrieved. The ML model is applied to a first batch of the training treatment plans to estimate a given set of geometric configurations. The output or result of the ML model is evaluated using a loss function to obtain feedback on the loss/utility of the current iteration. Based on this loss function, updated parameters for the ML model are computed. The ML model is then applied with the updated parameters to a second batch of training treatment plans to again estimate a given set of geometric configurations. Parameters of the ML model are again updated and iterations of this training process continue for a specified number of iterations or epochs or until a given convergence criteria has been met.

After each of the machine learning models is trained, new data, including one or more patient input parameters (e.g., a radiotherapy treatment plan data), may be received. The trained machine learning technique may be applied to the new data to generate geometric configurations.

Yet another approach in accordance with the present disclosure, is to apply reinforcement learning, which is a class of methods for sequential decision making, where an agent takes actions (at discrete points in time) in an environment to maximize a cumulative reward. As a method for isocenter generation, we can imagine each action to be the selection of one or a few isocenter locations that are then fixed. The reward could, for instance, be the value of Lightning's objective function, as described above. The learning enters because even though the environment is known, it is intractable to evaluate the rewards corresponding to all potential ways of placing isocenters. There are many different methods in reinforcement learning that apply to this situation, e.g., one could learn an approximation of the cumulative reward (value function) or learn a policy directly. Regardless, in order to act near optimally, the agent must reason about the long-term consequences of its actions (i.e., maximize future reward), although the immediate reward associated with this might be small. This property makes reinforcement learning well-suited for problems, such as sequential isocenter generation, that include a long-term versus short-term trade-off. Another advantage of reinforcement learning is that it's a natural fit when the length of the sequence is variable, something that otherwise causes problems for many machine learning algorithms. In practice, one could determine when to stop generating more isocenters when the expected future rewards are below a preset threshold.

Figure 3:
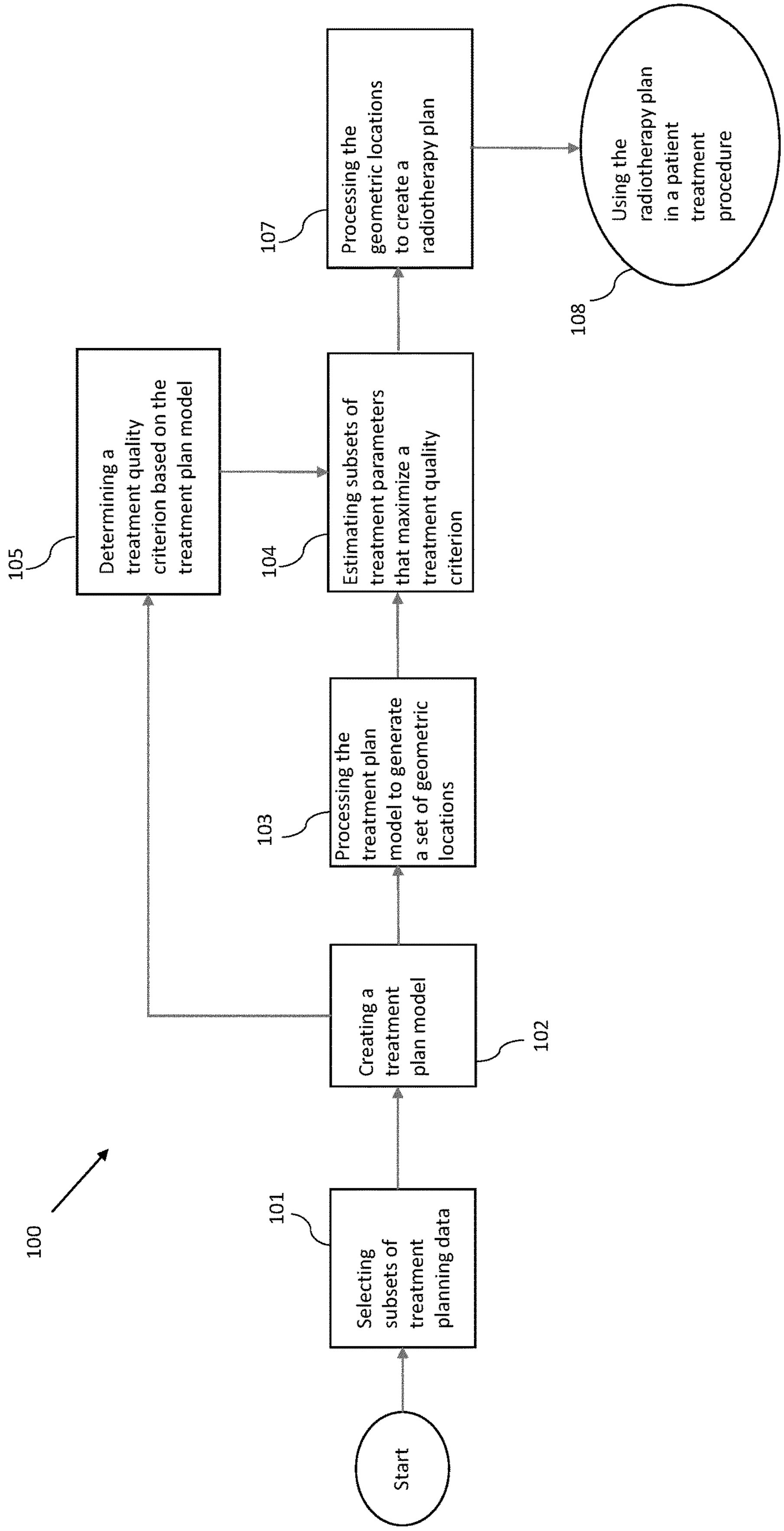
FIG. 3 shows a general method according to an embodiment of the present disclosure.
Figure 4:
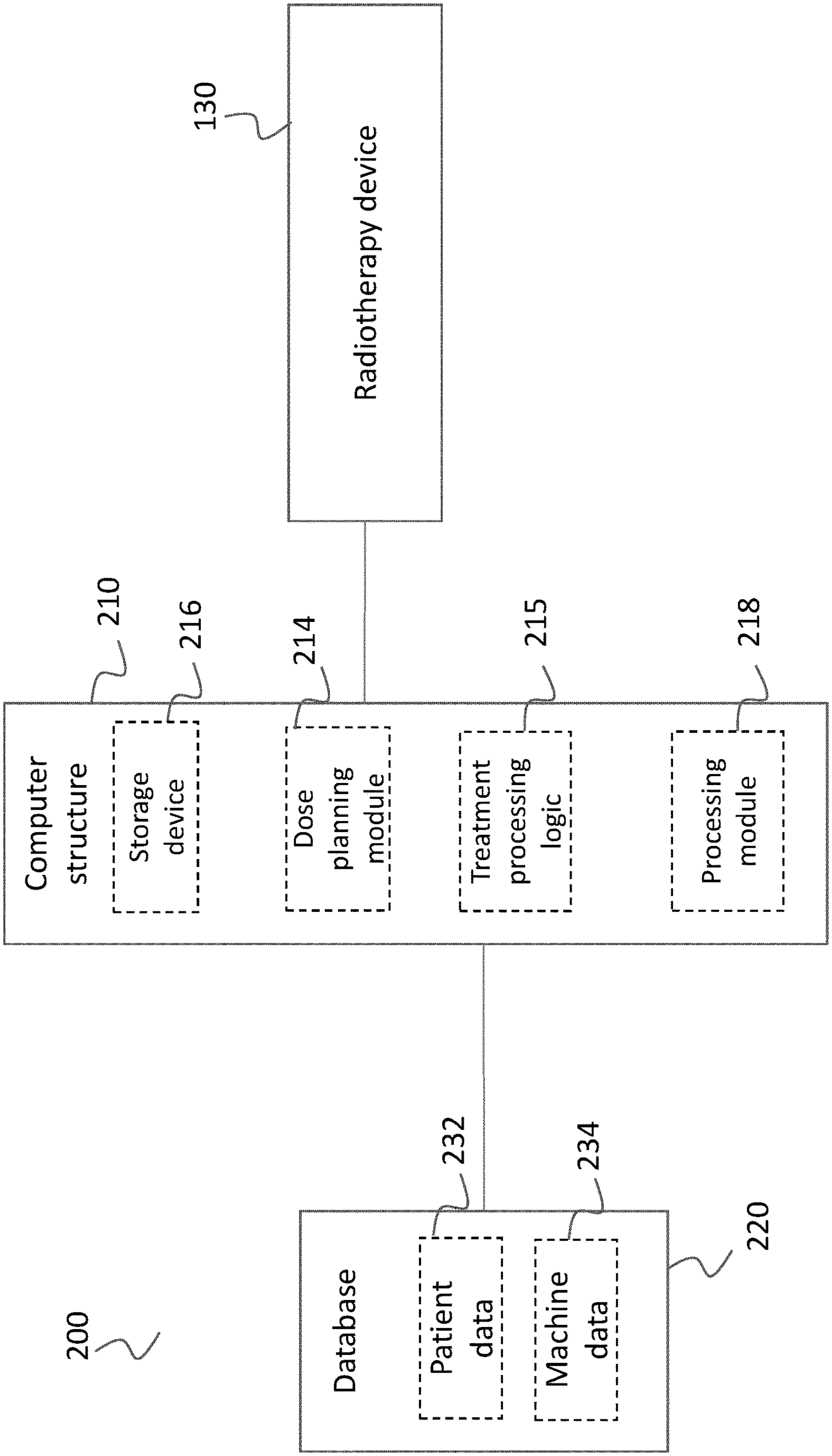
FIG. 4 shows an embodiment of a treatment planning computer structure according to the present disclosure.

With reference now to FIG. 3 a general and basic preferred embodiment of the present disclosure will be described. At the highest level, there is an abstract measure of plan quality that can't be accessed directly. But, it is modelled using a utility criterion or treatment quality criterion. A bit more concretely, for a preferred embodiment (Gamma Knife), the quality criterion would quantify the expected merit (over all planner preferences) of the combination of a dose distribution and the corresponding treatment complexity (mainly beam-on time). But it's infeasible to search over all dose distributions, which are parameterized by isocenter locations and corresponding beam-on times (i.e. the arguments). So, instead, arguments that maximize the utility or quality criterion are maximized in a two-stage procedure: first generating isocenter locations, then determining beam-on times with isocenter locations fixed.

However, in the general method, after the process is started, subsets of treatment related data are selected from the treatment planning data in step 101 and the step of determining a subset of the parameters based on a training set of treatment plan models may comprise optimizing a loss function. In embodiments of the present disclosure, the loss comprises at least one of the treatment quality criterion, a regularization term, a dose metric, a fluence metric, a merit function of a radiotherapy optimization problem or the optimal value of a radiotherapy optimization problem. Furthermore, the loss is differentiable or subdifferentiable, and the step of optimizing the loss function comprises evaluating gradients or subgradients of the loss function. According to embodiments of the present disclosure, the training set of treatment plan models includes treatment plan models created from non-clinical treatment related data. In embodiments of the present disclosure, the training set of treatment plan models comprises geometric configurations. According to embodiments of the present disclosure, the subsets of treatment related data in the training set of treatment plan models is restricted to the same kind of data the processed treatment plan model is based on. In embodiments of the present disclosure, the selected subsets of treatment related data from treatment planning data comprises at least one of medical images, structure sets, dose distributions, dose preferences, optimization preferences, medical condition, or geometric configurations. According to embodiments of the present disclosure, the treatment plan model is probabilistic.

Thereafter, at step 102, a treatment plan model is created from the subsets of treatment related data. The step of creating a treatment plan model may comprise using at least one of a model of radiation dose deposition or a model of treatment planning preferences for said treatment plan model.

At step 103, the treatment plan model is processed to generate a set of geometric configurations. The processing may include using a parameterized method including determining a subset of the parameters based on a training set of treatment plan models. According to embodiments of the present disclosure, the parameterized method may be organized in a directed graph.

At step 104, subsets of treatment parameters that maximize a treatment quality criterion are estimated in at least two phases. The treatment quality criterion is determined in step 105 based on the treatment plan model, and the treatment quality criterion may comprise at least one of a dose-based criterion and a radiotherapy optimization problem.

In step 106 the set of geometric configurations are processed to create a radiotherapy treatment plan. The step of processing the set of geometric configurations may comprise formulating a radiotherapy optimization problem based on the generated geometric configurations, and estimating a solution to said radiotherapy optimization problem using said generated geometrical configurations. The step of processing the set of geometric configurations may further comprise a first phase where geometric configurations are generated, and a second phase where the radiotherapy problem is solved for fixed geometrical locations.

In step 108, the radiotherapy treatment plan is used in a patient treatment procedure or a treatment action for the patient is determined based on the treatment plan and the treatment action is executed. The treatment quality criterion may reflect a quantification of expected merits of different combinations of treatment parameters for selected treatment planning variables and the selected treatment planning variables may include treatment planning preferences.

In embodiments of the present disclosure, the set of geometric configurations includes at least one of an isocenter location, a beam orientation or a seed position.

Further embodiments of the present disclosure include selecting subsets of treatment related data from treatment planning data, creating a treatment plan model from the subsets of treatment related data including defining a latent state model representing encoded geometrical locations, processing the treatment plan model to generate a set of geometric configurations, including determining isocenter locations in a target volume, determining a predicted dose distribution based on the generated set of geometric locations, evaluating the predicted dose distribution with respect to evaluation conditions, defining the evaluation conditions to include the selected subsets of treatment related data, for example, the evaluation conditions includes evaluating predicted dose distribution as output with respect to selected treatment data as input, and selecting the generated set of geometric locations if evaluation conditions are satisfied. However, the selected input could be a dose distribution (e.g. an ideal) to be matched by the predicted dose distribution, it might also be separated (boundary) conditions based on e.g. prescription dose, max OAR dose, geometry etc. that penalize any over respectively under shooting of predicted dose distribution. Note that the latter preferably allows for inputting disjointed sets of treatment data (possibly of different signs) unlike a dose distribution.

In embodiments of the present disclosure, the processing of the treatment plan model comprises receiving a set of geometric configurations and generating at least one new geometric configuration.

Yet other embodiments of the present disclosure comprise evaluating the utility criterion based on the generated geometric configuration and predetermined evaluation conditions, and, if conditions are not fulfilled, generating at least one further geometric location.

According to embodiments of the present disclosure the utility criterion or treatment quality criterion includes expected future values of utility criteria.

In embodiments of the present disclosure, the method for generating at least one new configuration uses at least one of optimal control, dynamic programming, or reinforcement learning.

Turning now to FIG. 6, a computer structure or software in which the method according to the present disclosure may be implemented will be described. The control console 210 (or software) may be included in a radiation therapy system 200 as shown in FIG. 6. As shown in FIG. 6, radiation therapy system 200 may include the control console 210, a database 220, a radiation therapy device 130. The computer structure or control console 210 may include hardware and software components to control radiation therapy device 130 and other equipment such as an image acquisition device (not shown) and/or to perform functions or operations such as treatment planning using a treatment planning software and dose planning, treatment execution, image acquisition, image processing, motion tracking, motion management, or other tasks involved in a radiation therapy process. The hardware components of control console 210 may include one or more computers (e.g., general purpose computers, workstations, servers, terminals, portable/mobile devices, etc.); processor devices (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); or other suitable hardware. The software components of control console 210 may include operation system software, application software, etc. For example, as shown in FIG. 6, control console 210 includes a dose planning computer structure or software 214 and a treatment planning/delivery software 215 that both may be stored in a memory/storage device of control console 210. Software 214 and 215 may include computer readable and executable codes or instructions for performing the processes described in detail in this application. For example, a processor device of control console 210 may be communicatively connected to a memory/storage device storing software to access and execute the codes or instructions. The execution of the codes or instructions may cause the processor device to perform operations to achieve one or more functions consistent with the disclosed embodiments.

The dose planning computer structure or software can be configured to execute the methods described herein, for example, the methods described with reference to FIG. 3.

As indicated above, control console 210 may be communicatively connected to a database 220 to access data. In some embodiments, database 220 may be implemented using local hardware devices, such as one or more hard drives, optical disks, and/or servers that are in the proximity of control console 210. In some embodiments, database 220 may be implemented in a data center or a server located remotely with respect to control console 210. Control console 210 may access data stored in database 220 through wired or wireless communication.

Database 220 may include patient data 232. Patient data may include information such as (1) imaging data associated with a patient anatomical region, organ, or volume of interest segmentation data (e.g., MRI, CT, X-ray, PET, SPECT, and the like); (2) functional organ modeling data (e.g., serial versus parallel organs, and appropriate dose response models); (3) radiation dosage data (e.g., may include dose-volume histogram (DVH) information); or (4) other clinical information about the patient or course of treatment.

Database 220 may include machine data 224. Machine data 224 may include information associated with radiation therapy device 130, image acquisition device 140, or other machines relevant to radiation therapy, such as radiation beam size, arc placement, on/off time duration, radiation treatment plan data, multi-leaf collimator (MLC) configuration, MRI pulse sequence, and the like.

Radiation therapy device 130 preferably includes a Leksell Gamma Knife®. However, in certain embodiments, the radiation therapy device 130 includes a linear accelerator, which irradiates a tumour with high-energy particles (e.g., photons, electrons, and the like). Still another radiation therapy device, a cyclotron, uses protons and/or ions.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMS, EEPROMs, magnetic or optical cards, or any type of media suitable for storing electronic instructions, each coupled to a computer system bus.

The order of execution or performance of the operations in embodiments of the present disclosure illustrated and described herein is not essential, unless otherwise specified. That is, the operations may be performed in any order, unless otherwise specified, and embodiments of the present disclosure may include additional or fewer operations than those disclosed herein. For example, it is contemplated that executing or performing a particular operation before, contemporaneously with, or after another operation is within the scope of aspects of the present disclosure.

Embodiments of the present disclosure may be implemented with computer-executable instructions. The computer-executable instructions may be organized into one or more computer-executable components or modules. Aspects of the present disclosure may be implemented with any number and organization of such components or modules. For example, aspects of the present disclosure are not limited to the specific computer-executable instructions or the specific components or modules illustrated in the figures and described herein. Other embodiments of the present disclosure may include different computer-executable instructions or components having more or less functionality than illustrated and described herein.

When introducing elements of aspects of the present disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the present disclosure in detail, it will be apparent that modifications and variations are possible without departing from the scope of aspects of the present disclosure as defined in the appended claims. As various changes could be made in the above constructions, products, and methods without departing from the scope of aspects of the present disclosure, it is intended that all matter contained in the above description and shown in the accompanying drawings shall be interpreted as illustrative and not in a limiting sense.

The invention claimed is:

1. A method for radiotherapy treatment planning comprising:

selecting subsets of treatment related data from treatment planning data;

creating a treatment plan model from the subsets of treatment related data;

processing the treatment plan model to generate a set of geometric configurations, wherein the processing includes estimating subsets of treatment parameters that maximize a treatment quality criterion, said treatment quality criterion being based on the treatment plan model; and processing the set of geometric configurations to create a radiotherapy treatment plan.

2. The method according to claim 1, wherein said treatment quality criterion reflects a quantification of expected merits of different combinations of treatment parameters for selected treatment planning variables.

3. The method according to claim 2, wherein said selected treatment planning variables include treatment planning preferences.

4. The method according to claim 1, wherein the step of creating a treatment plan model comprises using at least one of a model of radiation dose deposition or a model of treatment planning preferences for said treatment plan model.

5. The method according to claim 1, wherein the step of processing the set of geometric configurations further comprises formulating a radiotherapy optimization problem based on the generated geometric configurations; and estimating a solution to said radiotherapy optimization problem using said generated geometrical configurations.

6. The method according to claim 4, wherein the step of processing the set of geometric configurations further comprises a first phase where geometric configurations are generated, and a second phase where a radiotherapy optimization problem is solved for fixed geometrical locations.

7. The method according to claim 1, wherein the treatment quality criterion comprises at least one of a dose-based criterion and a radiotherapy optimization problem.

8. The method according to claim 1, where the processing includes using a parameterized method including determining a subset of the parameters based on a training set of treatment plan models.

9. The method according to claim 8, further comprising organizing the parameterized method in a directed graph.

10. The method according to claim 8, wherein the step of determining a subset of the parameters based on a training set of treatment plan models comprises optimizing a loss function.

11. The method according to claim 10, wherein the loss comprises at least one of the treatment quality criterion, a regularization term, a dose metric, a fluence metric, a merit function of a radiotherapy optimization problem or an optimal value of the radiotherapy optimization problem.

12. The method according to claim 10, wherein the loss is differentiable or subdifferentiable, and the step of optimizing the loss function comprises evaluating gradients or subgradients of the loss function.

13. The method according to claim 8, wherein the training set of treatment plan models includes treatment plan models created from non-clinical treatment related data.

14. The method according to claim 8, wherein the training set of treatment plan models comprises geometric configurations.

15. The method according to claim 8, wherein the subsets of treatment related data in the training set of treatment plan models is restricted to a same kind of data the processed treatment plan model is based on.

16. The method according to claim 1, wherein selected subsets of treatment related data from treatment planning data comprises at least one of medical images, structure sets, dose distributions, dose preferences, optimization preferences, medical condition, or geometric configurations.

17. The method according to claim 1, wherein the treatment plan model is probabilistic.

18. The method according to claim 1, wherein the set of geometric configurations includes at least one of an isocenter location, a beam orientation or a seed position.

19. The method according to claim 1, wherein selecting subsets of treatment related data from treatment planning data;

creating a treatment plan model from the subsets of treatment related data including defining a latent state model representing encoded geometrical locations;

processing the treatment plan model to generate a set of geometric configurations, including determining isocenter locations in a target volume;

determining a predicted dose distribution based on the generated set of geometric locations;

evaluating the predicted dose distribution with respect to evaluation conditions;

defining the evaluation conditions to include the selected subsets of treatment related data; and selecting the generated set of geometric locations if evaluation conditions are satisfied.

20. The method according to claim 1, wherein the processing of the treatment plan model comprises receiving a set of geometric configurations and generating at least one new geometric configuration by applying a machine learning model to the treatment plan model.

21. The method according to claim 20, further comprising evaluating a utility criterion based on the generated geometric configuration and predetermined evaluation conditions; and if conditions are not fulfilled, generating at least one further geometric location, wherein the machine learning model is trained using training data according to supervised or unsupervised learning techniques to minimize a loss function.

22. The method according to claim 21, wherein the utility criterion includes expected future values of utility criteria.

23. The method according to claim 20, wherein the method for generating at least one new configuration uses at least one of optimal control, dynamic programming, or reinforcement learning.

24. A non-transitory computer-readable medium having stored therein computer-readable instructions for a processor, wherein the instructions when read and implemented by the processor, cause the processor to: select subsets of treatment related data from treatment planning data; create a treatment plan model from the subsets of treatment related data; process the treatment plan model to generate a set of geometric configurations, wherein the processing includes estimating subsets of treatment parameters that maximize a treatment quality criterion in at least two phases, said treatment quality criterion being based on the treatment plan model; and process the set of geometric configurations to create a radiotherapy treatment plan.

* * * * *